US006896908B2

(12) United States Patent
Lloyd et al.

(10) Patent No.: US 6,896,908 B2
(45) Date of Patent: May 24, 2005

(54) WOOD PRESERVATIVE CONCENTRATE

(75) Inventors: Jeffrey D. Lloyd, Knoxville, TN (US); Jennifer L. Fogel, Los Angeles, CA (US)

(73) Assignee: U.S. Borax Inc., Valencia, CA (US)

( * ) Notice: Subject to any disclaimer, the term of this patent is extended or adjusted under 35 U.S.C. 154(b) by 280 days.

(21) Appl. No.: 10/002,101

(22) Filed: Nov. 14, 2001

(65) Prior Publication Data

US 2002/0146465 A1 Oct. 10, 2002

Related U.S. Application Data

(60) Provisional application No. 60/265,189, filed on Jan. 30, 2001.

(51) Int. Cl.$^7$ .................. A01N 59/00; A01N 59/14; A01N 59/16; A01N 59/20; A01N 37/02; B27K 3/52; B27K 3/16; B27K 3/34

(52) U.S. Cl. .................. 424/635; 424/600; 424/617; 424/630; 424/631; 424/632; 424/633; 424/634; 424/637; 424/638; 424/641; 424/657; 424/658; 424/659; 424/660; 424/686; 424/687; 424/700; 424/715; 424/716; 424/717; 424/719; 424/720; 424/721; 424/DIG. 10; 424/DIG. 11; 514/494; 514/499; 514/500; 514/553; 514/557; 106/18.3; 106/18.32; 106/15.05

(58) Field of Search .................. 424/600, 617, 424/630–635, 637–638, 641, 657–660, 686–687, 700, 715–717, 719–721, DIG. 10, DIG. 11; 514/494, 499, 500, 553, 557; 106/18.3, 18.32, 15.05

(56) References Cited

U.S. PATENT DOCUMENTS

| | | | |
|---|---|---|---|
| 2,194,827 A | 3/1940 | Gordon | |
| 2,573,253 A | 10/1951 | Farber | |
| 3,945,834 A | 3/1976 | Clark et al. | |
| 3,945,835 A | 3/1976 | Clark et al. | |
| 4,001,400 A | 1/1977 | Hager | |
| 4,038,086 A | 7/1977 | Clark et al. | |
| 4,061,500 A | 12/1977 | Hager | |
| 4,622,248 A | 11/1986 | Leach et al. | |
| 4,761,179 A | 8/1988 | Goettsche et al. | |
| 4,929,454 A | 5/1990 | Findlay et al. | |
| 5,207,823 A | 5/1993 | Shiozawa | |
| 5,342,438 A | 8/1994 | West | |
| 6,306,202 B1 | 10/2001 | West | |
| 6,387,300 B1 | 5/2002 | Bosserman | |

FOREIGN PATENT DOCUMENTS

| | | |
|---|---|---|
| DE | 3520313 A1 | 1/1986 |
| DE | 3805819 A1 | 9/1988 |
| EP | 0 238 413 A | 9/1987 |
| EP | 0 450 568 A3 | 10/1991 |
| EP | 0 636 461 A1 | 2/1995 |
| GB | 2 052 265 A | 1/1981 |
| GB | 2 082 912 A | 3/1982 |
| GB | 2 187 096 A | 9/1987 |
| JP | 56-25363 A | 6/1980 |
| JP | 63-159006 A | 7/1988 |
| JP | 3-140202 A | 6/1991 |
| JP | 6-336408 A | 12/1994 |
| WO | WO 95/27600 A1 | 10/1995 |
| WO | WO 00/09326 A1 | 2/2000 |
| WO | WO 01/70472 A1 | 9/2001 |
| WO | WO 01/79339 A1 | 10/2001 |

OTHER PUBLICATIONS

Kalnins, A., Ermuss, N., Svarcs, E., Ievins, A. and Podina, I., "New copper and boron–containing wood preservatives", Latv.PSR Zinat. Akad. Vestis, 1969, (8) pp. 64–66. (Chemical Abstract and English Translation only).

Pastors, N., Ermuss, N. and Kalnins, A., "Preservation of wood by copper borates. I. Toxicity of copper borates in relation to the wood–destroying fungus *Coniophora cerebella*", Chemical Abstracts, No. 79:88167. (Abstract only).

Johnson, B.R. and Gutzmer, D.I., "Ammoniacal Copper Borate: a New Treatment for Wood Preservation", Forest Products Journal, vol. 28, No. 2, Feb. 1978, pp. 33–36.

Kalnins A., Ermuss N. and Pastors N., "Study of preservatives containing copper and boron", Mikroorganizmy I Nizsh. Rast. Razrushiteli Materialov I Izdellii, M., pp. 176–180, 1979. (Russian and Chemical Abstract No. CA 93:97058).

Johnson, B.R., "Field trials with ammoniacal copper borate wood preservative", Forest Products Journal, vol. 33, No. 9, Sep. 1983, pp. 59–63.

Johnson, B.R. and Foster, D.O., "Preservative loss from stakes treated with ammoniacal copper borate", Forest Products Journal vol. 41, No. 9, Sep. 1991, pp. 37–38.

Lloyd, J.D., "Leaching of boron wood preservatives—a reappraisal", Proceedings of the British Wood Preservation and Damp Proofing Association Annual Convention, 1995.

Hedley, M., Wakeling R., Foster, J. and Patterson, B., "Performance of copper–chrome formulations in ground contact in five test sites in New Zealand", Proceedings of the 27th Annual Mtg of the Int'l Research Group on Wood Preservation, Doc. No. IRG/WP/96–30113, May 19–24, 1996.

Dev, I., Bagga, J.K., Misra, S.C. and Kumar, S., "Termite resistance and permanency tests on zinc–borate—an environmental friendly preservative", J. Timb. Dev. Assoc. (India), vol. XLIII, No. 2, Apr. 1997, pp. 10–15.

*Primary Examiner*—John Pak
(74) *Attorney, Agent, or Firm*—Kurt R. Ganderup

(57) ABSTRACT

This invention relates to a leach-resistant borate preservative for lignocellulosic-based products, providing resistance against insect and fungal attack for use in exterior and ground contact applications. The preservative compositions of this invention may be provided as a high strength liquid concentrate, suitable for transportation, storage and easy on-site dilution, or as a ready-to-use treatment solution. These wood preservative compositions include a borate preservative component and a co-biocidal metal fixative such as copper or zinc. The preservative compositions also contain volatile organic acid, free ammonia and ammonium salts to aid dissolution. Methods for the application of these preservative compositions to wood are also provided.

24 Claims, No Drawings

WOOD PRESERVATIVE CONCENTRATE

CROSS REFERENCE TO RELATED APPLICATIONS

This application claims the benefit under 35 U.S.C. 119(e) of U.S. Provisional Application No. 60/265,189, filed Jan. 30, 2001.

FIELD OF THE INVENTION

This invention relates to a leach-resistant borate preservative for lignocellulosic-based products, providing resistance against insect and fungal attack for use in exterior and ground contact applications. More particularly, this invention relates to a wood preservative composition which includes a borate preservative component and a cobiocidal metal fixative, and which can be produced as a pourable concentrate for subsequent on-site dilution for use in the treatment of wood products.

BACKGROUND OF THE INVENTION

Borates have been used as broad-spectrum wood preservatives for over 50 years. Their benefits include efficacy against most wood destroying organisms such as fungi, termites and wood-boring beetles, coupled with a low acute mammalian toxicity and low environmental impact. Soluble borates such as boric acid, borax and disodium octaborate tetrahydrate are well accepted as aqueous-based preservative systems for treating solid wood products for use in protected environments such as interior building applications and painted external joinery. However, because they are readily leached from treated wood when exposed to moisture, such as can occur in exterior or ground contact applications, they are not generally suitable for use in such exposed environments.

Copper chrome arsenate (CCA) is a leach-resistant wood preservative which has been used for may years to treat solid wood for exterior applications. However, such preservatives are facing increasing regulatory pressure as a result of environmental, health and safety problems due to the toxic nature of arsenic and chromium and suitable alternative systems have long been sought. Copper chrome boron (CCB) systems have been used, however the borate in these systems is leachable and over time all the borate will be removed, and the treated timber components will eventually decay, typically due to copper tolerant fungi. If the leaching of the borate components could be reduced in such systems, they would out-perform traditional preservatives such as CCA, as borate is a more effective fungicide than copper or zinc in the absence of leaching.

Solid zinc borate is added to wood composites during manufacture, because its inherent low solubility reduces leaching of the preservative in high moisture environments. However, such low solubility borates are not readily applied to solid lumber. Dev et al. (*J. Timb. Dev. Assoc.*, 1997) described a two-stage process for treating solid wood with zinc borate in which the wood is treated with solutions of borax and zinc chloride in two separate steps. However, the high cost of retreating and rehandling the wood makes the commercial use of such multi-stage processes unattractive.

Ammonia-based solutions have been proposed to solubilize metals such as zinc and copper in an attempt to fix borates in wood. U.S. Pat. No. 2,194,827 discloses an aqueous ammonia solution of copper, zinc and borate salts for the treatment of wood. Similarly U.S. Pat. No. 2,573,253 discloses a cupric ammonium borate solution which may be used for the preservation of wood. However, in order to achieve a high concentration of metals and borate in such solutions, it is necessary to use high concentrations of ammonia, resulting in excessive ammonia volatility and noxious fumes, creating undesirable worker exposure problems in large-scale operations.

JP Patent No. 56025363 discloses wood preservative compositions containing copper and zinc formate or acetate in combination with boric acid, sodium fluoride, starch and triethanolamine. Such amines can present problems as they allow more borate leaching and encourage mold growth on treated timber.

UK Application No. GB 2,187,096A discloses a preservative for wood made up of copper acetate and zinc acetate and optionally also containing a limited amount of boric acid (not more than 10%). However the boron is not effectively fixed and high levels of boric acid are avoided as it may reduce the leaching resistance of the metals.

WO 95/27600 discloses a preservative for treating wood including one or more copper salts and perhaps zinc salts of weak organic acids, an ammonium salt of a weak organic acid possibly mixed with an alkali metal salt of a weak organic acid, nitrite, plus perhaps other chemicals which may include boric acid and quaternary ammonium salts. Increased nitrite concentration improves fixation of the metals, but also tends to promote decomposition of the ammonium salt.

SUMMARY OF THE INVENTION

According to this invention, there are provided borate-based liquid preservative compositions for use in the treatment of solid wood products and other lignocellulosic materials. These compositions provide a leach resistant borate in combination with a co-biocidal metal fixative agent and is capable of providing long term protection against wood destroying organisms such as fungi and insects, and providing a leach-resistant borate-treated wood product which is suitable for use in exterior and ground contact applications. These compositions are substantially more environmentally friendly than widely used preservatives containing toxic elements such as chromium and arsenic. Furthermore, the preservative compositions of this invention may be provided as a high strength liquid concentrate, suitable for transportation, storage and easy on-site dilution, or as a ready-to-use treatment solution. This invention also provides methods for the application of these treatment solutions to wood for preservative treatment.

DETAILED DESCRIPTION OF THE INVENTION

The borate preservative concentrate compositions of this invention include a liquid concentrate preservative component, containing a high concentration of copper and/or zinc metal fixative dissolved in an aqueous ammoniacal and volatile organic acid solution, with a borate component suspended therein. The borate component, which is highly soluble in water, dissolves fully upon dilution of the preservative concentrate to produce a preservative solution suitable for use in the treatment of wood and other lignocellulose-based products. Furthermore, the borate and metal constituents, which serve as fixatives and cobiocides in the preservative compositions of this invention, become partially fixed in wood which is treated with the compositions, such that a preservative amount of both biocides is retained in the wood even after exposure to rigorous leaching conditions.

The preservative compositions of this invention offer a number of benefits. They are environmentally friendly, particularly in comparison with preservatives containing toxic components such as arsenic and chromium. The treatment solutions provide improved penetration into solid wood for effective wood treatment. They are capable of fixing sufficient levels of boron in wood to provide long term protection even against metal tolerant fungi, and even when exposed to leaching by water. They are deliverable as a high-strength pourable aqueous concentrate which is readily dissolved in water for easy on-site dilution and use at wood treatment facilities. They are not subject to major ammonia off-gassing like conventional ammonium hydroxide- or ammonia- based systems. They do not leave unsightly residue on the surface of the treated wood, as has been observed with the metal sulfate based systems.

Borate is the primary biocide in the preservative compositions of this invention, with copper and/or zinc providing both fixation for the borate and secondary supporting biocidal effects. The compositions of this invention also contain several complexing agents which are critical for keeping the copper and/or zinc metal component dissolved in the solution, and preventing premature reaction with the borate, both while the preservative is in the concentrate form and upon dilution. These complexing agents include volatile organic acid, free ammonia and ammonium salt. Carbonate salts and optional carbon dioxide are also useful in the dissolution of copper and zinc in the compositions of this invention. A volatile form of organic acid is used in order that it can be readily removed during drying of the wood, thus promoting better fixation of the preservative agents. The combination of a volatile organic acid and ammonia provides a high rate of metal dissolution without requiring excessive levels of ammonia in solution. The ammonium salt reduces the level of free ammonia which is needed for dissolution of the metals, thereby reducing ammonia off-gassing and making the treatment solution much less noxious and consequently easier to handle.

Suitable borates for use in the compositions of this invention include ammonium borate and alkali metal borates, such as, sodium borate. In particular, sodium metaborate, sodium tetraborate and disodium octaborate may be used. Borax (sodium tetraborate decahydrate), is particularly preferred, as it is readily suspended in the concentrated compositions of this invention and dissolves easily upon dilution of the concentrate with water.

The preservative metals suitable for use as fixatives in this system are copper and zinc, which may be used separately or in combination. These metals are solubilized in the presence of ammonia and/or ammonia-containing compounds along with carbonate and volatile organic acid. Copper gives better fixation in wood at lower levels and higher secondary biocidal performance, but zinc is less expensive and may be preferred in some applications as it is colorless. Copper or zinc carbonate is the preferred form as it is rapidly soluble and the carbonate aids in dissolution. Zinc oxide is also an effective source of zinc. However, copper oxide is less desirable as it is slower to dissolve. The elemental metals are also less desirable as they require the presence of an additional oxidizing agent. However, they can have cost advantages. Other metal salts, such as the copper or zinc sulfate and copper or zinc chloride leave undesirable deposits on the surface of the wood and would tend to promote corrosion of metals in contact with the treated wood such as metal fasteners when the treated wood is placed into service.

A volatile organic acid is essential for dissolving the metals, in order to minimize the amount of ammonia required in the final treatment solution and to maximize the concentration of copper and/or zinc in the liquid concentrate. Suitable volatile organic acids include acetic acid, formic acid, and propionic acid, which have boiling points below about 150° C. This permits effective removal of the acid in addition to ammonia, upon drying of the treated wood, allowing the formation of insoluble metal borate in the wood. Other non-volatile organic acids, such as citric acid, should not be used as they are not readily removed upon drying and their continued presence in the treated material promotes leaching of the borate and metal components from the treated wood.

Ammonia is provided in the preservative compositions of this invention both as free ammonia and as ammonium salt. Free ammonia may be introduced as ammonia gas or as aqueous ammonium hydroxide solution. The ammonium salt may be introduced in various forms such as ammonium carbonate, ammonium bicarbonate and ammonium borates.

The amount of borate used in the preservative solutions of this invention must be high enough to allow adequate fixation in the treated wood such that it will continue to provide effective protection against attack by wood destroying organisms even after exposure to substantial leaching conditions. The amount of the metal component (copper and/or zinc) which is required is to some extent inversely related to the amount of borate which is used—a reduction in the amount of metal causes a reduction in the leach-resistance of the borate component. However, the amount of the metal component which can be used is limited by the extent to which it can be dissolved in the concentrate. The weight ratio of borate (expressed as borax) to metal (expressed as metal oxide, CuO and/or ZnO) should be at least about 1:1 and may be as high as 7:1 or 8:1. Preferably this ratio is at least about 2:1 up to about 4:1. The preferred levels of the biocidal components in the treatment solutions after dilution of the concentrate according to this invention, using copper as the metal biocide component, are in the range of about 2% borate, expressed as sodium tetraborate decahydrate (borax), and 0.7% copper, expressed as copper oxide (CuO), to about 1.2% borate, and 1% copper oxide. If copper is replaced partially or completely by zinc, a somewhat higher level of the metal component may be required for adequate fixation and subsequent protection of the wood. For example, if copper is replaced completely by zinc, preferred levels of zinc in the treatment solution range from about 1.2% zinc, expressed as zinc oxide (ZnO), in combination with about 2% borate to about 1.7% zinc and 1.3% borate.

A substantial benefit of the present system is the ability to provide the preservative in the form of a high-strength pourable aqueous concentrate. This allows for ease of shipping and storage, ready for on-site dilution, as needed. However, being a pourable liquid, it can be mixed and dissolved in water more easily than powders or other solid materials. It dissolves quickly and requires minimal mixing equipment. The concentrate is stabilized by the interaction of several different complexing agents, including free ammonia, ammonium salt and volatile organic acid all in an aqueous base, rather than relying on the complexing power of a single agent such as ammonia. Therefore, higher concentrations of the transition metal can be dissolved in the aqueous concentrate and less ammonia is required than in conventional ammonia-based systems, resulting in much less noxious off-gassing of ammonia from the treatment solutions and even from the treated wood making it easier and safer to handle after the treatment is completed.

The preferred levels of the biocidal components in the concentrated preservative compositions according to this invention are generally 10–12 times higher than the treatment solution concentrations, depending upon the dilution ratio which is desired. The preservative concentrate may contain between 2 and 12% by weight of the metal component, expressed as the metal oxide (CuO and ZnO), and preferably at least 5%. The borate concentration may range from about 3 to 45% by weight borate (expressed as borax, i.e. sodium tetraborate decahydrate), and preferably at least 15%. For example, a typical copper-containing preservative concentrate could contain from about 20–24% by weight borate (expressed as borax equivalent) in combination with 7–9% copper oxide equivalent to about 13–16% borate in combination with 10–12% copper oxide equivalent. A higher strength concentrate according to the invention, such as Formulation III described in Example 8, could contain between about 24 and 30 weight % borate in combination with about 10–12 weight % copper oxide equivalent.

It may be preferred in some situations to make the concentrate without the borate and add the borate component to the preservative solution after the concentrate is diluted to the appropriate strength for wood treatment.

The concentration of the complexing agents are dependent on each other and also on the concentration of the metal constituent which must be dissolved. For example, the molar ratio of volatile organic acid to the metal (copper or zinc or a combination of both) should be preferably in the range of about 0.1–0.4:1. The molar ratio of total ammonia to the metal should be preferably at least about 3:1 up to about 6:1 or 7:1. The molar ratio of free ammonia to ammonia as ammonium salt should be at least about 0.3:1, preferably around or above 1:1, most preferably around or above 2:1, up to about 3:1 or 4:1. A sufficient amount of ammonia must be present to fully complex the remaining metal and to completely neutralize the organic acid, and an excess of ammonia may be desired to ensure stability of the concentrated solution in the event of some minor evaporation during transfer and dilution. A typical concentrate according to the invention which contains in the range of about 7–12 weight % metal oxide (CuO and/or ZnO) could contain a variable range of complexing agents, such as about 0.8–1.6 weight % volatile organic acid, about 7–10 weight % free ammonia, about 2–4% ammonia as ammonium salt, and about 13–16 weight % carbonate.

The pH of the preservative treatment solution is preferably between about 9.5 and 11.5. The concentrated solution may become unstable and precipitate from solution during storage or during the treatment process if the pH is less than 8.0. The selection of an alkali metal borate as the borate component, such as borax or sodium metaborate as opposed to boric acid for example, facilitates neutralization of the organic acid and provides greater borate fixation.

The preservative compositions of this invention may be prepared as a ready-to-use treatment solution, or alternatively may be prepared as a concentrate for later dilution prior to use in a treatment process. Preparation of a concentrate for later dilution is preferred if the preservative requires shipping or storage prior to use, whereas direct preparation at a lower concentration may be acceptable if it is being prepared at the wood treatment site for immediate use. If the preservative is prepared as a concentrate for later dilution, the borate, which does not completely dissolve in the concentrated solution, may be incorporated as an undissolved solid which will go into solution upon dilution, prior to use in a wood treatment application, or alternatively may be added later upon dilution when it becomes entirely soluble. If the borate is included as part of the concentrate, sodium tetraborate decahydrate is the preferred form of the borate, as it is more effectively suspended and dispersed in the concentrate, thus leading to easier mixing and dissolution at the time of dilution and use. Sodium tetraborate pentahydrate is less preferred as it tends to become more consolidated in the concentrate, and is therefore somewhat harder disperse and dissolve upon dilution.

The concentrate may be prepared by first dissolving the metal component in a small amount of water using the various complexing agents. The borate is then added and mixed in but remains partially undissolved in the concentrate. The borate becomes completely dissolved when the concentrate is diluted in water prior to use. Alternatively, the borate component may be added later to the diluted solution.

The preferred method for dissolving the metal component in the concentrate is to first combine in a small amount of water a source of free ammonia, such as an aqueous ammonium hydroxide solution, with the volatile organic acid. In particular, it is best to add the volatile organic acid to the water, followed by the ammonia. After the volatile organic acid is completely integrated into the solution, a source of the metal co-biocide, such as copper carbonate, and an ammonium salt, such as ammonium bicarbonate, are added and mixed until the metal component is completely dissolved in the concentrate. The borate may be mixed into the concentrate anytime thereafter, or alternatively may be added after dilution of the concentrate.

The concentrated solution may be formulated over a broad temperature range. The preferred temperature is between 15° and 30° C. (60° to 80° F.). Factors to consider are the freezing points of the components and the loss of ammonia and volatile organic acid at high temperatures due to evaporation.

To achieve a solution ready for treatment, the concentrate is diluted to attain the desired borate and metal fixative retention in the wood. The level of preservative treatment which is required for adequate protection of a lignocellulosic-based product may vary broadly depending on the nature of the substrate, its geographic location, method of application, its end use, and the nature of the attack to be prevented. Generally though, it is desirable to achieve a borate loading of at least 0.3% borax decahydrate equivalent in the wood on a dry weight basis for interior, non-termite hazard applications and at least 2.3% borax decahydrate equivalent for exterior or termite hazard applications.

The pourable aqueous concentrate compositions of this invention offer several significant benefits over dry preservative formulations and unconcentrated liquid formulations. For example it is less expensive to ship a concentrate compared to unconcentrated liquid formulations, and a concentrate requires less storage space. Furthermore, it is generally faster and easier to prepare the final treatment solution by dilution of an aqueous concentrate compared with preparation from a solid (e.g. granular or powdered) concentrate or from multiple separate components. In particular, the preferred forms of the concentrate of this invention, made with sodium tetraborate decahydrate (borax), are especially stable and readily dispersed and dissolved in water for ease of use. In addition, preparation of a treatment solution from a solid formulation or from multiple chemical components is likely to require more capital investment in processing equipment than simple dilution of a pourable aqueous concentrate.

The method of treating wood or other lignocellulosic-based materials with the preservative solutions of this invention involves impregnating the wood with the preservative solution, followed by drying of the wood. For optimum performance, vacuum and/or pressure techniques are preferably used to impregnate wood. The preservative solution may alternatively be applied to the lignocellulosic substrate by a variety of well-known means, such as dipping, soaking, spraying, brushing. Following impregnation, the wood or other lignocellulosic-based product is dried such that substantially all of the volatile components of the preservative composition are removed. Kiln drying or other heat treatment helps metal fixation and overall performance. This will help to fix the preservative components in the wood and reduce the tendency to mobilize and leach out when the wood is exposed to moisture.

The resultant treated wood products are protected against decay by wood destroying organisms. The preservative is resistant to leaching by moisture, making it suitable for use in exterior or ground contact applications.

EXAMPLES

The following examples illustrate the novel preservative compositions and methods of this invention.

Example 1

As series of laboratory scale tests were run in which wood blocks were treated with various preservative treatment solutions, then subjected to rigorous leaching conditions, followed by a decay test. A detailed description of these tests follows.

Preservative Solutions:

A total of seventeen (17) different copper and zinc treatment solutions were tested, each containing 1.5% sodium tetraborate pentahydrate (borax pentahydrate). Eleven (11) of the formulations contained a copper or zinc carbonate salt and either formic, acetic or propionic acid, according to the methods and compositions of this invention. The other six (6) tests utilized comparative formulations containing either the copper or zinc carbonate salt in combination with citric acid, not included in the invention, or copper sulfate without any organic acid, also outside the invention. The seventeen treatment solutions were then used to treat wood blocks.

Preparation of Organic Acid-Containing Solutions:

For each preservative solution, 154.52 grams of 28–30% ammonium hydroxide solution (=28–30% $NH_3$) and 0.13 moles of organic acid (i.e. 5.83 g formic acid, 7.6 g acetic acid, 9.38 g propionic acid, or 26.62 g citric acid) were mixed with 159.56 grams of deionized water. Then 95.9 grams of ammonium bicarbonate and either 63.4 grams of copper carbonate ($Cu_2(OH)_2CO_3$) containing 0.573 moles Cu, or 68.7 grams of zinc carbonate ($5ZnO.2CO_3.4H_2O$) containing 0.573 moles Zn, were added and mixed until all of the copper or zinc had dissolved, to produce a concentrate. The concentrates were diluted and sodium tetraborate pentahydrate was added and dissolved to produce a final treatment solution containing 1.5% by weight sodium tetraborate pentahydrate (1.96% borax decahydrate equivalent) and either 0.5%, 0.75% or 1.0% by weight cupric oxide (CuO) equivalent for the copper-containing solutions or 0.75% zinc oxide (ZnO) equivalent for the zinc-containing solutions.

Preparation of Copper Sulfate-Containing Solutions:

Two copper sulfate solutions were prepared (0.75% and 1.0% CuO). Copper sulfate pentahydrate, $CuSO_4.5H_2O$, (14.29 g. for the 0.75% solution and 19.05 g. for the 1.0% solution) was added to 60 g. of 28–30% ammonium hydroxide solution and 9 g. sodium tetraborate pentahydrate. This was then made up to a total of 600 g. with water.

The seventeen preservative treatment solutions are listed in Table 1.

TABLE 1

TREATMENT SOLUTIONS

| Treatment Solution No. | % Borax Pentahydrate | % CuO or % ZnO | Metal added as | Organic Acid |
|---|---|---|---|---|
| 1 | 1.5 | 0.75 | $5ZnO.2CO_3.4H_2O$ | Formic Acid |
| 2 | 1.5 | 0.75 | $5ZnO.2CO_3.4H_2O$ | Acetic Acid |
| 3* | 1.5 | 0.75 | $5ZnO.2CO_3.4H_2O$ | Citric Acid |
| 4 | 1.5 | 0.5 | $Cu_2(OH)_2CO_3$ | Formic Acid |
| 5 | 1.5 | 0.5 | $Cu_2(OH)_2CO_3$ | Acetic Acid |
| 6 | 1.5 | 0.5 | $Cu_2(OH)_2CO_3$ | Propionic Acid |
| 7* | 1.5 | 0.5 | $Cu_2(OH)_2CO_3$ | Citric Acid |
| 8 | 1.5 | 0.75 | $Cu_2CO_3(OH)_2$ | Formic Acid |
| 9 | 1.5 | 0.75 | $Cu_2CO_3(OH)_2$ | Acetic Acid |
| 10 | 1.5 | 0.75 | $Cu_2CO_3(OH)_2$ | Propionic Acid |
| 11* | 1.5 | 0.75 | $Cu_2CO_3(OH)_2$ | Citric Acid |
| 12* | 1.5 | 0.75 | $CuSO_4$ | None |
| 13 | 1.5 | 1.0 | $Cu_2CO_3(OH)_2$ | Formic Acid |
| 14 | 1.5 | 1.0 | $Cu_2CO_3(OH)_2$ | Acetic Acid |
| 15 | 1.5 | 1.0 | $Cu_2CO_3(OH)_2$ | Propionic Acid |
| 16* | 1.5 | 1.0 | $Cu_2CO_3(OH)_2$ | Citric Acid |
| 17* | 1.5 | 1.0 | $CuSO_4$ | None |
| 18** | 0.0 | 0.0 | water only | water only |

(*= comparative formulation)
(**= control)

Wood Blocks:

Wood blocks were prepared from Southern yellow pine, solely from sapwood with similar grain orientation. They were ensured to have identical dimensions of 19×19×19 mm (¾-inch cube). None of the wood samples had undergone prior treatment. Each wood block was individually weighed prior to treatment.

Wood Treatment:

Wood samples were each submerged in one of the treatment solutions and held down by weights to guarantee complete immersion. A total of sixteen replicates were treated with each solution, and eighteen replicates were treated with water to serve as controls. Samples were vacuum pressure treated at approximately −26" Hg for thirty minutes, approximately 140 Psi for sixty minutes, and at atmospheric pressure for thirty minutes. Wet weights of the blocks were recorded to determine the calculated uptake. All samples were subsequently dried at 60° C. for two hours and 40° C. overnight, using a circulating air oven. Wood blocks which had been treated with different solutions were kept separate throughout the remainder of the experimental procedure. Four blocks from each solution set were analyzed without leaching and the remaining blocks were subjected to leaching according to the following procedure.

Leaching Tests:

Leaching was carried out using the American Wood Preserver's Association Standard E10-91 leach test (Standard Method of Determining the Leachability of Wood Preservatives). It is a standardized laboratory leaching procedure designed with waterborne preservatives in mind. The treated wood samples were submerged in deionized water (50 ml×the number of wood blocks) and vacuum pressure treated at 100 mm Hg for thirty minutes, the weights were removed and the blocks were left for six hours. The same volume of water was replaced at twenty four, forty eight, and every forty eight hours thereafter for a period of fourteen days. Four blocks from each set were removed after six days, and fourteen days. The last remaining four blocks from each treatment set were kept for fungal decay analysis.

Retention Analysis:

Following leaching and drying, the samples chosen for retention analysis were cut into eight smaller pieces and refluxed in 1.0N HCl for two hours. The resulting solution was filtered and analyzed for % borate, % CuO and % ZnO content using the ICP (Inductively Coupled Argon Plasma Emission Spectroscopy).

Fungal Decay Test:

Decay tests were carried out according to the AWPA E10-91 standard decay test procedure. AWPA E10-91 is used to determine the minimum amount of preservative that is effective in preventing decay in a selected species of wood by selected fungi under optimum laboratory conditions. The test procedures are described below.

The samples from each set were sealed in plastic bags and gamma irradiated at a level of 2.0 Mrad using a $^{60}$Co source to ensure sterilization prior to monoculture decay testing. Decay testing was carried out according to AWPA E10 using copper tolerant brown rot fungi.

An 80:20 respective combination of Whitney's Farms Bonsai Soil Mix and Whitney's Farms Washed Sand, was found to give a water holding capacity of 21.3% with a pH of 5.0–5.5 and was therefore utilized in the decay study. The bonsai soil mix and the washed sand were air dried and passed through a US No. 6 sieve. Animal jars (dimensions: height=7 cm, diameter=9 cm) were prepared for the fungal decay test by adding 74.0 g (addition of this water achieves a 130% moisture content in the soil) of deionized water and 190.0 g of the soil mixture. Four sapwood feeder strips were placed on top of the soil in each jar and then the jars with their lids on loosely were placed into the autoclave for sterilization at 120° C. for thirty minutes. Inoculation of the jars with a mature culture of *Coniophora puteana* (copper tolerant brown rot—Basidiomycotina) was carried out in such manner that the fungal inoculum rested on the soil and was in contact with each feeder strip. Inoculated jars were then incubated at 22° C. +/−2° C. until the mycelium fully covered the feeder strips.

Using aseptic technique, the gamma irradiated wood blocks were then placed on top of the feeder strips in the following manner: three blocks from each treatment set and one control block were placed into each jar, the remaining blocks were placed into a jar lacking a control. The lids to the jars were loosely screwed on to allow for air exchange, and were then incubated at 22°C. +/−2° C. for a period of twelve weeks.

Results

The leach and decay test results are summarized in Table 2.

TABLE 2

LEACH AND DECAY RESULTS

| Treatment Solution | | Leach Results: Wood Analyses after Leaching | | Decay Results: |
|---|---|---|---|---|
| No. | Description | % Borax as Pentahydrate | % Metal as CuO or ZnO | % Wt. Loss |
| 1 | 0.75% ZnO/Formic | 0.024 | 0.75 | 0.5 |
| 2 | 0.75% ZnO/Acetic | 0.015 | 0.73 | −0.17 |
| 3 | 0.75% ZnO/Citric | 0.004 | 0.50 | 1.88 |
| 4 | 0.5% CuO/Formic | 0.042 | 0.41 | −0.38 |
| 5 | 0.5% CuO/Acetic | 0.032 | 0.39 | 2.18 |
| 6 | 0.5% CuO/Propionic | 0.034 | 0.46 | 3.46 |
| 7 | 0.5% CuO/Citric | 0.000 | 0.22 | 6.85 |
| 8 | 0.75% CuO/Formic | 0.07 | 0.63 | −0.12 |
| 9 | 0.75% CuO/Acetic | 0.08 | 0.69 | 0.66 |
| 10 | 0.75% CuO/Propionic | 0.11 | 0.81 | 0.46 |
| 11 | 0.75% CuO/Citric | 0.02 | 0.35 | 8.59 |
| 12 | 0.75% CuO/CuSO$_4$ | 0.11 | 0.77 | 1.17 |
| 13 | 1.0% CuO/Formic | 0.13 | 0.89 | 0.26 |
| 14 | 1.0% CuO/Acetic | 0.14 | 0.97 | −0.21 |
| 15 | 1.0% CuO/Propionic | 0.14 | 0.94 | 0.56 |
| 16 | 1.0% CuO/Citric | 0.04 | 0.45 | 7.68 |
| 17 | 1.0% CuO/CuSO$_4$ | 0.19 | 1.09 | 0.32 |
| 18 | Water (controls) | 0.00 | 0.00 | 24 |

Formulations containing the volatile organic acids provided significantly better retention of both the borate and the metal component (copper or zinc) at all levels of addition compared with the formulations containing citric acid. The retention of borate increased significantly as copper loading increased, illustrating the fixative benefits of copper in this system. Formulations containing copper sulfate provided roughly the same level of borate retention as the volatile organic acids, at comparable copper and zinc loading levels. Copper provided better borate retention than zinc at comparable metal loadings (0.75% metal oxide).

Increasing the copper concentration from 0.5% CuO up to 0.75–1.0% CuO in the treatment solution significantly improved the leach-resistance of the borate component in the preservative compositions of this invention, while the leach-resistance of the borate component in the preservative compositions containing citric acid remained relatively low. A borax pentahydrate concentration of 1.5% together with copper concentrations of 0.75% and 1.0% CuO in the volatile organic acid-containing treatment solutions of this invention provided excellent control of decay by the copper tolerant fungus (less than 1.0% weight loss), even after exposure of the samples to very rigorous leaching conditions. The citric acid formulations with copper provided poor control of the copper tolerant fungi, experiencing 6–9% weight loss in the decay test. A borate retention of around 0.05% after leaching provided an apparent toxic threshold for protection of wood against the copper tolerant fungi. The controls, with no preservative added, averaged 24% weight loss in the decay tests.

Example 2

A 500-gram concentrated copper preservative was prepared using formic acid as follows. Formic acid (5.83 g.) and 28–30% ammonium hydroxide solution (154.52 g.) were mixed with 159.56 g. deionized water. Then 95.9 grams of ammonium bicarbonate and 63.4 g. copper carbonate (Cu$_2$(OH)$_2$CO$_3$) were added and mixed until all of the copper had dissolved to produce a concentrate totaling 479.21 g.

Fifty (50) gram samples of this concentrate were added into each of two flasks. Sodium tetraborate pentahydrate (12.75 g.) was added to one flask and sodium tetraborate decahydrate (16.6 g.) was added to the other. These two different sodium tetraborates are essentially the same chemical form of borate, except that the decahydrate form has more water of crystallization. These borate-containing concentrates contained about 7.0–7.5 weight % free ammonia (as ammonium hydroxide), about 3.2–3.4 weight % ammonia as ammonium salt (ammonium bicarbonate), and about 14–15 weight % carbonate (as copper carbonate and ammonium bicarbonate). The borate-containing concentrates were each diluted with water to produce a 1.5% borax pentahydrate (1.96% borax decahydrate equivalent) concentration in an 850 g. final treatment solution containing 0.5% copper oxide.

It was observed that, when sodium tetraborate pentahydrate was added, a solid formed at the bottom of the flask which was difficult to dissolve when the concentrate was subsequently diluted in water to the working treatment solution concentrations. However, when sodium tetraborate decahydrate was added, a pourable volume of discreet particles persisted indefinitely at the bottom of the flask. This was easily dissolved when the concentrate was diluted with water to the working solution concentrations. The use of sodium tetraborate decahydrate allowed the concentrates to be diluted to working concentration much more easily than sodium tetraborate pentahydrate. The reason for the improved performance using the decahydrate form is not known for certain, but may reflect its greater stability in aqueous solution, whereas the pentahydrate may react with the water converting to decahydrate, and in the process recrystallize into a solid mass which is then harder to suspend and dissolve in aqueous media.

Example 3

A borate-containing preservative concentrate was prepared as follows. Formic acid (100.86 g.) and 28–30% ammonium hydroxide solution (2673.35 g.) were combined with 2760.54 g. water. Once the formic acid was completely integrated into the solution, 1659.16 g. ammonium bicarbonate and 1096.88 g. copper carbonate ($Cu_2(OH)_2CO_3$) were added. When all of the contents were fully dissolved, 1840.17 g. sodium tetraborate decahydrate was added to produce a pourable concentrate having the following approximate composition:

1.0 wt. % formic acid
15.8 wt. % ammonium hydroxide
16.4 wt. % ammonium bicarbonate
7.4 wt. % copper oxide (CuO) equivalent
18.2 wt. % sodium tetraborate decahydrate and containing about 7.7 weight % free ammonia (as ammonium hydroxide), about 3.5 weight % ammonia as ammonium salt (ammonium bicarbonate), and about 15.3 weight % carbonate (as copper carbonate and ammonium bicarbonate).

Example 4

A borate-containing preservative concentrate was prepared as follows. Formic acid (129.29 g.) and 28–30% ammonium hydroxide solution (3426.68 g.) were combined with 3538.45 g. water. Once the above contents were mixed, 1523.07 g. zinc carbonate ($5ZnO \cdot 2CO_3 \cdot 4H_2O$) and 2126.7 g. ammonium bicarbonate were added. The solution was mixed for several hours and then filtered. Sodium tetraborate decahydrate (1839.58 g.) was added to the clear solution to form a concentrate having the following approximate composition:

1.0 wt. % formic acid
16.3 wt. % ammonium hydroxide
16.9 wt. % ammonium bicarbonate
8.2 wt. % zinc oxide (ZnO) equivalent
14.6 wt. % sodium tetraborate decahydrate and containing about 7.9 weight % free ammonia (as ammonium hydroxide), about 3.6 weight % ammonia as ammonium salt (ammonium bicarbonate), and about 15.9 weight % carbonate (as zinc carbonate and ammonium bicarbonate).

Example 5

Comparative

An attempt was made to prepare a copper sulfate concentrate corresponding to the copper sulfate treatment solutions described in Example 1, for subsequent dilution to a 0.5% CuO and 1.96% borax decahydrate (1.5% borax pentahydrate equivalent). However, it was not possible to make a workable concentrate of this formulation, as it was not possible to put that much copper sulfate into solution. Copper carbonate and copper oxide gave even poorer results than copper sulfate.

Example 6

Full scale-type treatment trials using a vacuum/pressure wood treatment cylinder were performed to assess commercial performance characteristics of various treatment solutions and any potential difficulties which might arise during wood treatment. Visible assessments were also made of the treated lumber after drying in order to gauge aesthetic quality. The treatment solutions evaluated include dilutions of the formic acid formulations of Examples 4 and 5 and, for comparative purposes, treatment solutions containing copper sulfate and/or zinc sulfate together with borate in an ammonium hydroxide formulation that did not contain any organic acid or ammonium bicarbonate. Large batches (94 liters each) of the following treatment solutions were prepared and used in full scale-type treatment trials:

Solution A—The preservative concentrate of Example 3 was diluted with water by a factor of about 9.5:1 to produces a treatment solution with a target concentration of 1.96% borax decahydrate and 0.75% CuO equivalent.

Solution B—After the wood treatment trial on Solution A was completed, one third of the solution was removed and replaced with borax decahydrate and water to produce a treatment solution with a target concentration of 1.96% borax decahydrate and 0.5% CuO.

Solution C—After the wood treatment trial on Solution B was completed, one half of the solution was removed and replaced with borax decahydrate and water to produce a treatment solution with a target concentration of 1.96% borax decahydrate and 0.25% CuO.

Solution D—The preservative concentrate of Example 4 was diluted with water by a factor of about 6:1 to produce a treatment solution with a target concentration of 1.96% borax decahydrate and 1.0% ZnO equivalent.

Solution E—A copper sulfate treatment solution was prepared to target levels of 0.5% CuO equivalent and 1.96% borax decahydrate using the copper sulfate preparation procedure of Example 1. Borax decahydrate was substituted for borax pentahydrate. Approximately 7% of the total working solution was ammonium hydroxide solution which was need to dissolve the copper sulfate pentahydrate.

Solution F—The copper sulfate preparation procedure of Example 1 was used to prepare a copper and zinc sulfate treatment solution containing target levels of 0.45% CuO equivalent (using copper sulfate pentahydrate), 1.15% ZnO equivalent (using zinc sulfate heptahydrate) and 1.96% borax decahydrate equivalent (using borax pentahydrate).

Solution G—After the wood treatment trial on Solution F was completed, one third of the solution was removed and replaced with borax pentahydrate and water to produce a treatment solution with a target concentration of 1.5% borax pentahydrate (1.96% borax decahydrate equivalent), 0.30% CuO equivalent and 0.76% ZnO equivalent.

Solution H—After the wood treatment trial on Solution G was completed, one half of the solution was removed and replaced with borax pentahydrate and water to produce a treatment solution with a target concentration of 1.5% borax pentahydrate (1.96% borax decahydrate equivalent), 0.15% CuO equivalent and 0.38% ZnO equivalent.

Preparation and dilution of the concentrations proceeded smoothly. Sodium tetraborate decahydrate formed a mobile solid in the concentrate that was easily dissolved when diluted with water to working solution concentrations. A sample of each treatment solution was taken for chemical analysis using ICP (Inductively Couples Argon Plasma Emission Spectroscopy). The target retentions of the treatment solutions were slightly high but comparatively precise. Results of the ICP analysis of the treatment solutions for % Borax (sodium tetraborate decahydrate), % CuO and % ZnO are given in Table 3, along with the target levels for each solution concentration.

TABLE 3

ICP ANALYSIS OF THE TREATMENT SOLUTIONS

| Solution | % Borax Decahydrate | | % CuO | | % ZnO | |
|---|---|---|---|---|---|---|
| | ICP | Target | ICP | Target | ICP | Target |
| A | 2.25 | 1.96 | 0.89 | 0.75 | 0.0 | 0.0 |
| B | 2.41 | 1.96 | 0.64 | 0.5 | 0.0 | 0.0 |
| C | 2.41 | 1.96 | 0.35 | 0.25 | 0.0 | 0.0 |
| D | 2.16 | 1.96 | 0.00 | 0.00 | 1.2 | 1.0 |
| E | 2.34 | 1.96 | 0.56 | 0.5 | 0.0 | 0.0 |
| F | 2.19 | 1.96 | 0.48 | 0.45 | 1.24 | 1.15 |
| G | 2.19 | 1.96 | 0.33 | 0.30 | 0.84 | 0.76 |
| H | 2.21 | 1.96 | 0.17 | 0.15 | 0.44 | 0.38 |

Wood Samples:

Southern Yellow Pine wood samples were cut from 2"×4" lumber to lengths of 20 inches. The samples contained mostly sapwood with some heartwood portions, however other imperfections, such as sapstain and knots, were avoided. None of the wood samples had undergone prior treatment.

Treatment of Samples:

The treatment solutions according to this invention were prepared from concentrates containing ammonium hydroxide, formic acid, copper or zinc carbonate, ammonium bicarbonate and borax. Comparative treatment solutions contained ammonium hydroxide, copper and optionally zinc carbonates, and sodium tetraborate penta- or decahydrate. All of the final working solutions were prepared to total 94 L in volume. Each solution contained 1.96% borax decahydrate (or equivalent, 1.5% borax pentahydrate). A total of 4 wood samples were treated with each treatment solution.

Each wood sample was individually weighed and labeled prior to treatment. For each treatment the samples were placed into the cylinder and vacuum treated at ~660 mmHg for thirty minutes. The treatment solution was introduced into the cylinder under vacuum conditions and then changed to pressure. The samples were pressure treated at 140psi for one hour. After treatment the solutions were drained from the cylinder and samples underwent an additional vacuum treatment of ~660 mmHg for 10 minutes. The wood samples were removed from the cylinder and their wet weights were recorded to allow for the calculation of uptake. After each set of similar treatment solutions the cylinder and operational storage vessel were thoroughly rinsed with water and a small amount of ammonium hydroxide to ensure that no contamination was left before the next set of treatment solutions were used. A drying schedule of 60° C. for two days followed by air temperature until fully dry was used for all samples.

Results

There were no mechanical or equipment difficulties and no obvious treatment plant problems resulting from the treatment solutions, such as corrosion, premature precipitation in cylinder or operation storage vessel, or sludging due to reacting with wood extractives.

The sulfate-containing preservative systems with no organic acid or ammonium bicarbonate (solutions E–H) required more ammonium hydroxide in the working solution in order to dissolve the copper or zinc metal, resulting in greater amounts of ammonia off-gassing in the treatment process. An exhaust fan was needed to remove ammonia gas from solutions E–H, and it was difficult to handle this treated wood due to the continued ammonia off-gassing. The formic acid-containing treatment solutions (A–D) required only a small amount of ammonium hydroxide and did not cause significant ammonia off-gassing.

A visible assessment was made of the wood samples after drying on their appearance. The formic acid treatment solutions (A–D) produced smooth surfaces with no residue on the surface of the treated wood, in either a clear wood (for zinc-containing preservatives) or slightly green tinted wood (for copper-containing formulations). The sulfate-containing treatment solutions (E–H) caused unsightly crystal or powder residue on the surface of the wood. Treatment solution E created many crystals on the surface. Samples treated with treatment solutions F–G were covered heavily with a bluish white powder.

Example 7

A penetration test was conducted, comparing the effective penetration of a treatment solution according to this invention with penetration by several commercially available treatment solutions. Dry, green, and green incised Douglas Fir samples were treated with solutions of ammoniacal copper quaternary ammonium compound (ACQ), copper chrome arsenic (CCA), or a preservative composition according to this invention containing copper carbonate, formic acid and borax (CFB). The depth of penetration with each of these treatment solutions was evaluated visually and by chemical analysis. The test procedures are described below.

Materials and Methods

Wood Samples:

Dry, green, and green incised Douglas Fir (*Pseudotsuga menziesii*) nominal 2"×4" pieces of lumber were used. One stick of each was cut to lengths of 5 inches, so that each sample for comparison was from the exact same 2×4. None of the wood samples had undergone prior treatment.

Treatment Solutions:

Samples were treated with ammoniacal copper quaternary ammonium compound, modified Type D solution (ACQ-D manufactured by Chemical Specialties Inc, but obtained as a ready-for-use commercial solution), copper chrome arsenic Type C (CCA-C ready-for-use commercial Wolmanac® solution, manufactured by Hickson Corporation/Arch), or a copper carbonate, formic acid, borax (CFB) formulation according to this invention which was prepared as follows:

CFB Treatment Solution:

First a concentrate was made containing copper formate and sodium tetraborate decahydrate. The copper formate was produced by first combining 228.8 g of water and 8.4 g of formic acid, then adding 221.6 g of ammonium hydroxide solution (28–30% $NH_3$). Combining the chemicals in this order reduced the premature release of volatile components. When completely mixed 90.9 g of copper (II) carbonate dihydroxide (55% Cu) and 137.6 g of ammonium hydrogen carbonate were added. When the components were fully dissolved 138 g of sodium tetraborate decahydrate was added. The borate did not fully dissolve but thickened the concentrate and dispersed evenly through it. This concentrate was then diluted with water to a treatment solution totaling 3000 g, and containing 1.95% copper oxide and 4.6% sodium tetraborate decahydrate.

Treatment:

Each wood sample was end sealed using ABS polymer dissolved in acetone and individually weighed prior to treatment. Wood samples were submerged in the treatment solutions and held down by weights to guarantee complete immersion. The treatment was carried out by a vacuum provided at ~660.4 mm Hg for one hour, then pressure at ~140 Psi for two hours. Wet weights were recorded and the calculated increases in weight showed similar levels of solution uptake between each of the dry samples, each of the green samples, and each of the green incised samples. The samples were dried at room temperature until they reached a level of less than 20% moisture content.

Penetration Analysis:

After treatment was completed, four centimeters were cut off one of the end of each sample to observe treatment solution penetration visually. Heartwood penetration was then measured with a rule, and a photograph was taken. Chemical analysis of the heartwood penetration was also performed. Approximately one and a half centimeters were cut off of each side of the samples to ensure that only penetration into the wide face was measured (radial penetration), without contamination from the sides or tangential penetration (converting the 2×4's into 2×3's). Then using a micrometer the depth of the samples were measured. A Lion Miter Trimmer was used to cut very thin slices off the heartwood face of the sample, and the new depth of the sample was measured to determine the depth of the slice. This was repeated until a long way past the visual signs of penetration disappeared.

Borate Retention Analysis:

The slices of the samples were broken into smaller pieces for retention analysis. The pieces were refluxed in 1. ON HCl for two hours. The resulting solution was filtered and analyzed for % BAE (boric acid equivalent retention), % $As_2O_3$, % $CrO_3$, and % CuO content utilizing the ICP (Inductively Coupled Plasma Atomic Emission Spectroscopy).

Results

Penetration results based on visual inspection are shown in Table 4.

TABLE 4

Penetration Results-Visual Inspection

| | Penetration (mm) | | |
|---|---|---|---|
| Wood Condition | CCA | ACQ | CFB |
| Dry | 4[A] | 3 | 7.5 |
| Green | 1.5[B] | 1[B] | 6 |
| Green incised | 2[B] | 2 | 9 |

[A]Split
[B]End grain penetration

Penetration results based on chemical analysis was determined to the depth where at least 0.005% of an active ingredient was found. These results are summarized in Table 5.

TABLE 5

Penetration Results-Chemical Analyses

| | Chemical | Penetration (mm) | | |
|---|---|---|---|---|
| Wood Condition | Analysis | CCA | ACQ | CFB |
| Dry | CuO | 5.44[A] | 4.4 | 7.57 |
| Dry | BAE | — | 5.71 | 17.32 |
| Green | CuO | 4.79[B] | 6.42[B] | 11.23 |
| Green | BAE | — | 6.42[B] | 11.23 |
| Green incised | CuO | 3.18[B] | 7.84 | 11.96 |
| Green incised | BAE | — | 5.4 | 5.33 |

[B]Some samples may have experienced a slight amount of end grain penetration through the end grain seals.
[A]Also observed was a split, that may have given greater penetration than otherwise.

Discussion and Conclusion

Visual observations showed greater penetration of the copper borate solution than ACQ or CCA. This was confirmed by the chemical analysis. The active ingredients in the copper borate solution gave better penetration in all samples of Douglas fir: dry, green, and green incised. Analysis of the dry Douglas fir showed that both copper (~8 mm) and borate (~17 mm) of the CFB solution penetrated further than all elements (4–6 mm) of ACQ and CCA. Similar results were seen in the green and green incised Douglas fir. The CFB solution provided better penetration of both elements in all three types of samples.

From the results gained it can be concluded that the CFB solution according to this invention gives better penetration of it's wood preserving elements in Douglas fir heartwood than either ACQ or CCA. These results were evident in the dry, green, and green incised Douglas fir tested. It is noteworthy that greater penetration was not achieved by analysis for the incised material. This is not normally the case, and this piece was obviously of an unusually high refractory (penetration resistant) nature. Penetration of the non-incised timber may be increased enough to eliminate the step of incising when treating Douglas fir with the preservative system according to this invention. Eliminating this step of the procedure would be a significant time and cost saving in lumber processing.

Example 8

Additional copper-containing concentrates were prepared in an attempt to increase the copper content and decrease water content in the concentrates of the invention. A concentrate was prepared using the same ratio of solubilizing components (water, formic acid, ammonium hydroxide solution and ammonium bicarbonate) as were used in making the copper-containing concentrate of Example 2. However, a larger amount of copper carbonate was added, up to the maximum amount of copper which would dissolve in the concentrate. The composition of this concentrate was as follows:

Formulation I 79.78 g. (31.8%) water 2.92 g. (1.2%) formic acid 77.26 g. (30.8%) ammonium hydroxide solution (28–30% $NH_3$)

47.95 g. (19.1%) ammonium bicarbonate 43.04 g. (17.2%) copper carbonate

This provided an effective concentrate composition in which all of the copper was fully dissolved. Formulation I contained 11.8% CuO equivalent. Unsuccessful attempts were made to reduce the water in this composition by removing one half to one fourth of the water component. These formulations are listed below:

| Comparative Formulations: | | |
|---|---|---|
| ½ Water Formulation | ¼ Water Formulation | Component |
| 19.95 g. | 29.92 g. | water |
| 1.46 g. | 1.46 g. | formic acid |
| 38.63 g. | 38.63 g. | ammonium hydroxide solution (28–30% NH$_3$) |
| 23.97 g. | 23.97 g. | ammonium bicarbonate |
| 21.52 g. | 21.52 g. | copper carbonate |

These formulations containing ½ to ¼ of the water found in Formulation I were undesirable because the copper did not fully dissolve. However, it was found that the water could be reduced by ½ by also increasing the formic acid and ammonium hydroxide by 50%. It was also found that the copper could be further increased under these conditions. The result was Formulation II, shown below:

Formulation II 19.95 g. (14.7%) water
2.19 g. (1.6%) formic acid
57.84 g. (42.5%) ammonium hydroxide solution (28–30% NH$_3$)
23.97 g. (17.6%) ammonium bicarbonate
32.11 g. (23.6%) copper carbonate This provided an effective high-strength copper-containing concentrate in which all of the copper was fully dissolved and the concentrate could still also be diluted to working strength (for a wood treatment solution) without precipitation of any of the components. However, an attempt to remove the remaining water from Formulation II by further increasing the formic acid and ammonium hydroxide was unsuccessful. This formulation is shown below:

Comparative Formulation:

0 g. water
2.92 g. formic acid
77.05 g. ammonium hydroxide solution (28–30% NH$_3$)
23.97 g. ammonium bicarbonate
32.11 g. copper carbonate The above formulation did not provide complete dissolution of the components as a concentrate and did not dissolve properly, resulting in further precipitation of the components. A borax-containing concentrate was prepared based on Formulation II, above. This is shown below as Formulation III.

Formulation III 19.95 g. (10.8%) water
2.19 g. (1.2%) formic acid
57.84 g. (31.2%) ammonium hydroxide solution (28–30% NH$_3$)
23.97 g. (12.9%) ammonium bicarbonate
32.11 g. (17.3%) copper carbonate
49.4 g. (26.6%) sodium tetraborate decahydrate Formulation III is a preferred embodiment of the invention. It contains about 9.8 wt. % B$_2$O$_3$ equivalent, about 11.8 wt. % CuO equivalent and about 9.4 wt. % ammonia as ammonium hydroxide. This concentrate contains more copper and less water than earlier versions of the concentrate. It also contains a lower ratio of both free ammonia and ammonium salt to copper. Dilution of this concentrate at a dilution factor of about 13.6:1 would yield a treatment solution containing roughly 1.96% borax and 0.91% CuO equivalent, which should be capable of providing excellent protection to treated wood based on the leach experiments described in Example 1.

Various changes and modifications of the invention can be made and, to the extent that such variations incorporate the spirit of this invention, they are intended to be included within the scope of the appended claims.

What is claimed is:

1. An aqueous-based preservative concentrate for use in treating lignocellulosic-based materials comprising:
    (a) a borate selected from the group consisting of ammonium borate and alkali metal borate, wherein the concentration of said borate, expressed as sodium tetraborate decahydrate equivalent, comprises at least about 15% by weight of the concentrate,
    (b) a source of metal, wherein said metal is selected from the group consisting of copper, zinc and a combination thereof, and wherein the concentration of said metal, expressed as metal oxide equivalent (CuO and/or ZnO), comprises at least about 5% by weight of the concentrate,
    (c) a volatile organic acid or salt thereof, wherein said acid has a boiling point below about 150° C., and wherein the molar ratio of the volatile organic acid to said metal is in the range of about 0.1 to 0.4:1,
    (d) a source of free ammonia,
    (e) an ammonium salt,
    (f) a source of carbonate, and
    (g) water
    wherein the weight ratio of the borate, expressed as sodium tetraborate decahydrate, to the metal, expressed as metal oxide, is at least 1:1, the concentration of total ammonia, including the sum of free ammonia and ammonia as ammonium salt, is at least 5% by weight of the concentrate, and wherein said concentrate has a pH greater than 8.0.

2. The preservative concentrate according to claim 1 wherein the volatile organic acid is selected from the group consisting of formic acid, acetic acid and propionic acid.

3. The preservative concentrate according to claim 1 wherein the ammonium salt is selected from the group consisting of ammonium carbonate and ammonium bicarbonate.

4. The preservative concentrate according to claim 1 wherein the source of free ammonia is selected from the group consisting of ammonia gas and ammonium hydroxide.

5. The preservative concentrate according to claim 1 wherein the borate is a sodium borate.

6. The preservative concentrate according to claim 1 wherein the borate is sodium tetraborate decahydrate.

7. The preservative concentrate according to claim 1 wherein the source of carbonate is selected from the group consisting of carbonate salts, carbon dioxide and carbonic acid.

8. The preservative composition according to claim 1 wherein the pH of the composition is between about 9.5 and 11.5.

9. The preservative composition according to claim 1 wherein the weight ratio of the borate, expressed as sodium tetraborate decahydrate, to the metal, expressed as metal oxide, is at least about 2:1.

10. The preservative concentrate according to claim 1 wherein the metal is fully dissolved and the borate is partially dissolved and partially dispersed in the concentrate.

11. The preservative concentrate according to claim 1 wherein the source of metal is selected from the group consisting of metal carbonate, metal oxide, metal hydroxide and elemental metal.

12. The preservative concentrate according to claim 1 wherein the source of metal is selected from the group consisting of copper carbonate, zinc carbonate and zinc oxide.

13. The preservative concentrate according to claim 1 comprising about 9.8% by weight $B_2O_3$ equivalent, about 11.8% by weight CuO equivalent and about 9.4% by weight ammonia as ammonium hydroxide.

14. The preservative concentrate according to claim 13 wherein the borate is sodium tetraborate decahydrate and the source of metal is copper carbonate.

15. A method for preserving wood comprising the steps of: (a) diluting the preservative concentrate according to claim 1 with water to form a preservative treatment solution: (b) applying the treatment solution to wood so that the solution penetrates into the wood; (c) drying the wood so that there is deposited in the wood a biocidal amount of borate and a co-biocidal metal fixative.

16. The method according to claim 15 wherein the treatment solution is applied to wood using vacuum and/or pressure techniques.

17. The method according to claim 15 wherein the treated wood is kiln dried or heat treated.

18. A treated wood product produced by the method of claim 15 whereby said wood product contains a biocidal amount of borate and a co-biocidal metal fixative, thereby making the wood resistant to attack by wood destroying organisms.

19. A treated wood product according to claim 18, having an outer surface, wherein said outer surface is substantially free of surface deposits from the preservative treatment solution.

20. A preservative wood treatment solution comprising:
(a) a borate selected from the group consisting of ammonium borate and alkali metal borate, wherein the concentration of said borate, expressed as sodium tetraborate decahydrate equivalent, is in the range of between about 1.2 and 2% by weight of the solution,
(b) a source of metal, wherein said metal is selected from the group consisting of copper, zinc and a combination thereof, and wherein the concentration of said metal, expressed as metal oxide equivalent (CuO and/or ZnO), is in the range of between about 0.5 and 1.5% by weight of the solution,
(c) a volatile organic acid or salt thereof, wherein said acid has a boiling point below about 150° C., and wherein the molar ratio of the volatile organic acid to said metal is in the range of about 0.1 to 0.4:1,
(d) a source of free ammonia,
(e) an ammonium salt,
(f) a source of carbonate, and
(g) water
wherein the weight ratio of the borate, expressed as sodium tetraborate decahydrate, to the metal, expressed as metal oxide, is at least 1:1, and wherein said solution has a pH greater than 8.0.

21. A preservative wood treatment solution according to claim 20 wherein the metal is copper and the concentration of copper, expressed as percent CuO is between about 0.75% and about 1.0% by weight.

22. A method for preparing an aqueous-based borate- and metal-containing preservative concentrate comprising the following steps:
(a) adding a volatile organic acid or salt thereof, wherein said acid has a boiling point below about 150° C., and wherein the molar ratio of the volatile organic acid to said metal is in the range of about 0.1 to 0.4:1, and a source of free ammonia into water and mixing until an integrated mixture is obtained;
(b) adding a source of said metals, wherein the metal is selected from the group consisting of copper, zinc and a combination thereof, and wherein the concentration of said metal, expressed as metal oxide equivalent (CuO and/or ZnO), comprises at least about 5% by weight of the borate- and metal-containing preservative concentrate, and an ammonium salt to the integrated mixture, wherein at least one of the source of metal and ammonium salt is added in the form of a carbonate or bicarbonate thereby providing a source of carbonate, and mixing until the metal is completely dissolved to form a metal-containing concentrate; and
(c) adding borate selected from the group consisting of ammonium borate and alkali metal borate, wherein the concentration of said borate,expressed as sodium tetraborate decahydrate equivalent, comprises at lease about 15% by weight of the borate- and metal-containing preservative concentrate, and mixing into the metal-containing concentrate until all of the borate has dissolved or dispersed,
thereby forming an aqueous-based borate- and metal-containing preservative concentrate having a weight ratio of borate, expressed as sodium tetraborate decahydrate, to metal, expressed as metal oxide, of at least 1:1 a concentration of total ammonia, including the sum of free ammonia and ammonia as ammonium salt, of at least 5% by weight, and a pH of greater than 8.0.

23. The method according to claim 22 wherein the borate is sodium tetraborate decahydrate.

24. The method according to claim 22 wherein the metal-containing concentrate is shipped or stored before adding the borate.

* * * * *